US 6,712,771 B2

(12) United States Patent
Haddock et al.

(10) Patent No.: US 6,712,771 B2
(45) Date of Patent: Mar. 30, 2004

(54) TEMPERATURE SENSING CATHETER

(75) Inventors: Thomas F. Haddock, Ann Arbor, MI (US); William W. O'Neill, Grosse Pointe Farms, MI (US)

(73) Assignee: Accumed Systems, Inc., Ann Arbor, MI (US)

( * ) Notice: Subject to any disclaimer, the term of this patent is extended or adjusted under 35 U.S.C. 154(b) by 0 days.

(21) Appl. No.: 09/882,889

(22) Filed: Jun. 15, 2001

(65) Prior Publication Data

US 2001/0053882 A1 Dec. 20, 2001

Related U.S. Application Data

(60) Provisional application No. 60/211,995, filed on Jun. 16, 2000.

(51) Int. Cl.$^7$ ................................................ A61B 5/00
(52) U.S. Cl. ....................................................... 600/549
(58) Field of Search ................................ 600/474, 549, 600/393, 505, 585, 481, 434, 435; 374/148, 141, 166, 179

(56) References Cited

U.S. PATENT DOCUMENTS

| | | | |
|---|---|---|---|
| 5,237,996 A | 8/1993 | Waldman et al. ............ 128/642 |
| 5,345,938 A | 9/1994 | Nishiki et al. ......... 128/660.04 |
| 5,433,708 A | * 7/1995 | Nichols et al. ............. 604/113 |
| 5,771,895 A | 6/1998 | Slager ................... 128/662.06 |
| RE35,880 E | 8/1998 | Waldman et al. ............ 600/374 |
| 5,810,802 A | 9/1998 | Panescu et al. ................ 606/31 |
| 5,871,449 A | 2/1999 | Brown ........................ 600/474 |
| 5,924,997 A | 7/1999 | Campbell .................... 600/549 |
| 5,935,075 A | 8/1999 | Casscells et al. ........... 600/474 |
| 6,023,638 A | 2/2000 | Swanson ..................... 600/510 |
| 6,200,312 B1 | * 3/2001 | Zikorus et al. ................ 606/32 |
| 6,245,026 B1 | 6/2001 | Campbell et al. ........... 600/549 |
| 2002/0048310 A1 | * 4/2002 | Heuser ....................... 374/141 |

FOREIGN PATENT DOCUMENTS

| | | | |
|---|---|---|---|
| EP | 0 856 278 A2 | 12/1997 | |
| EP | 0 943 293 A1 | 3/1999 | |
| GR | 1003178 B | 7/1999 | ............ A61B/5/00 |
| WO | WO 92/20290 | 11/1992 | |
| WO | WO 00/13603 | 3/2000 | |
| WO | WO 01/74263 A1 | 10/2001 | ............ A61B/18/08 |
| WO | WO 02/15780 A1 | 2/2002 | ............ A61B/5/00 |

OTHER PUBLICATIONS

"Coronary Thermosensor Basket Catheter: a Low–Cost Tool for Thermal Detection of Atherosclerotic Plaques," from www.hotplaque.com website Mar. 2002, author unknown.
M. Naghavi, S. Siadaty, J. Willerson, W. Casscells, "Thermosensor Catheter; a Nitinol Shape Memory Basket Catheter to Measure Temperature of Vessel Wall with Continuous Blood Floow," Mar. 2000.
"CCL Device to Reduce Chances of Heart Attack," Business Weekly, Jun. 2002, author unknown.
Dr. S. Vereye, et al. "In Vivo Temperature Heterogeneity of Atherosclerotic Plaques is Determined by Plaque Composition," Basic Science Reports, Mar. 2002.

* cited by examiner

Primary Examiner—Charles Marmor, II
(74) Attorney, Agent, or Firm—Gifford, Krass, Groh, Sprinkle, Anderson & Citkowski, PC

(57) ABSTRACT

A thermal sensing catheter finds particular utility in detecting and isolating unstable arterial plaque. Miniaturized temperature sensors, preferably in the form of microthermistors, are embedded into expandable presentation elements disposed at the distal end of a catheter. The sensors may then be deployed to measure the surface temperature of the inner wall of coronary arteries or other vessels at multiple sites to identify sites of elevated temperature indicative of unstable plaque. The presentation elements may assume a "hand" type design or an alternate basket-type structure. A plurality of thermal sensors are embedded into the sides of polymeric or metallic sensing elements which expand out from the centerline of a catheter toward the inner vessel walls.

14 Claims, 7 Drawing Sheets

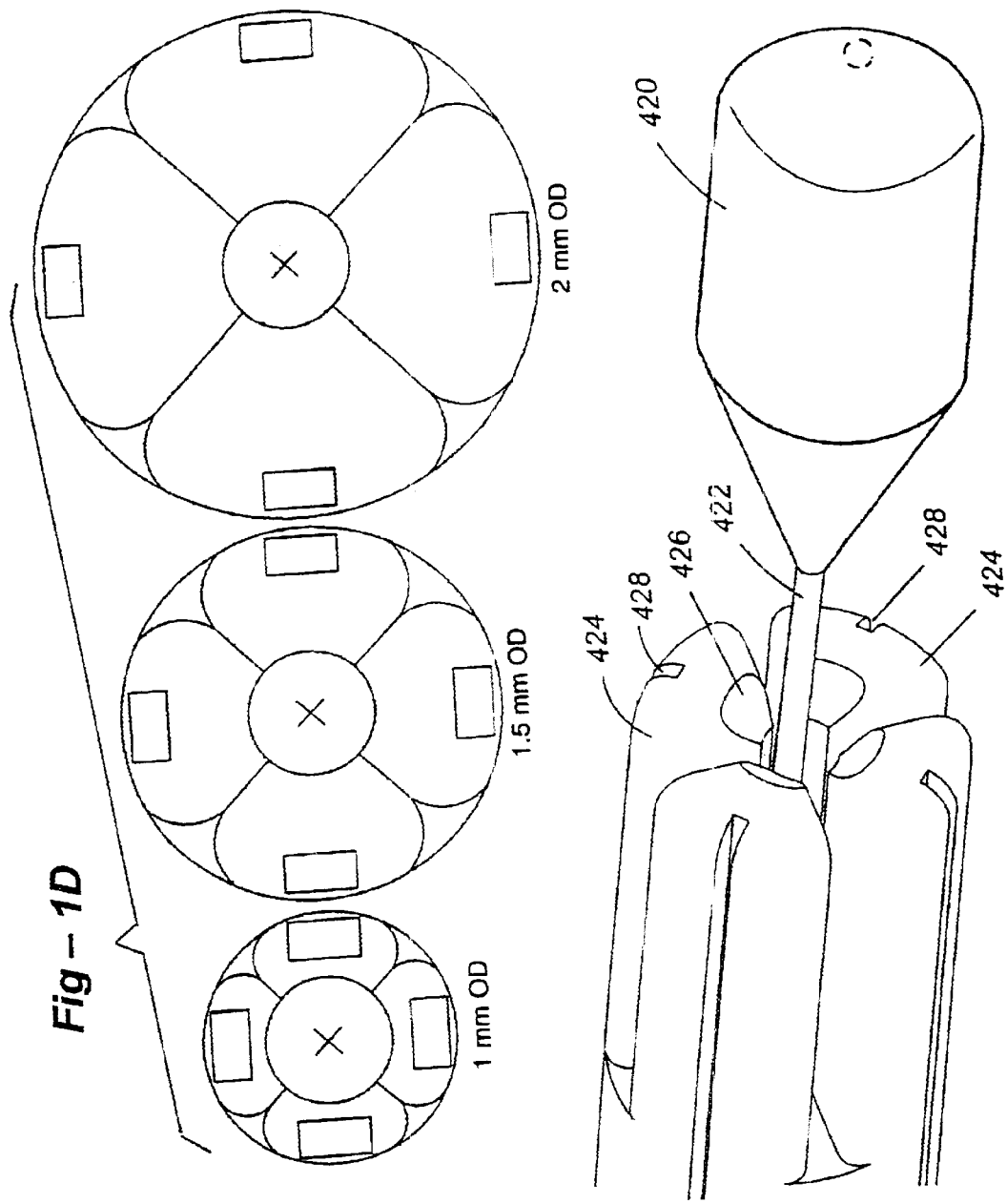

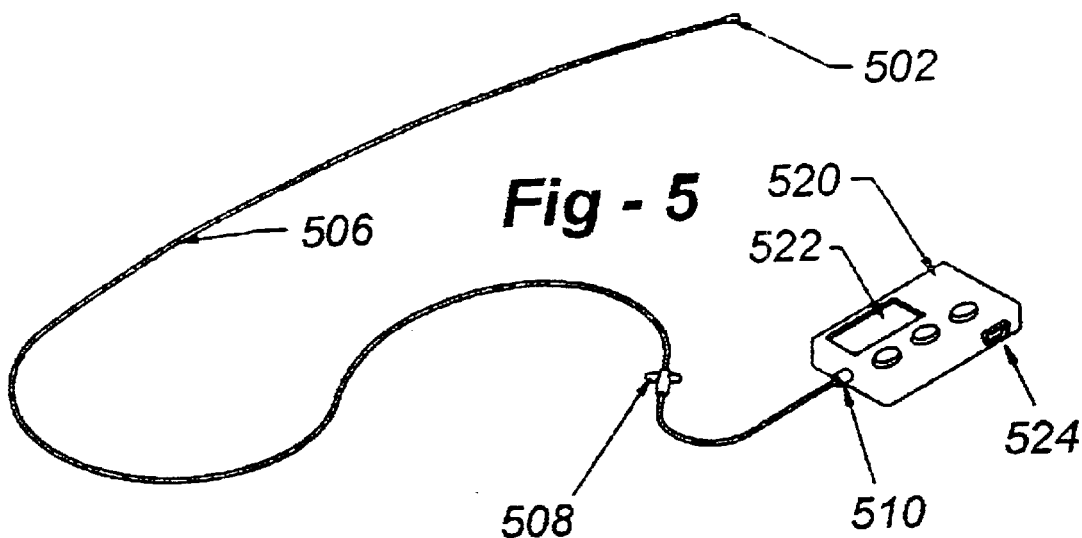
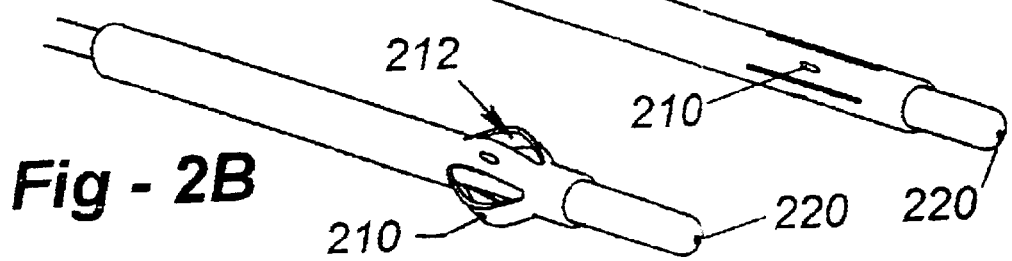

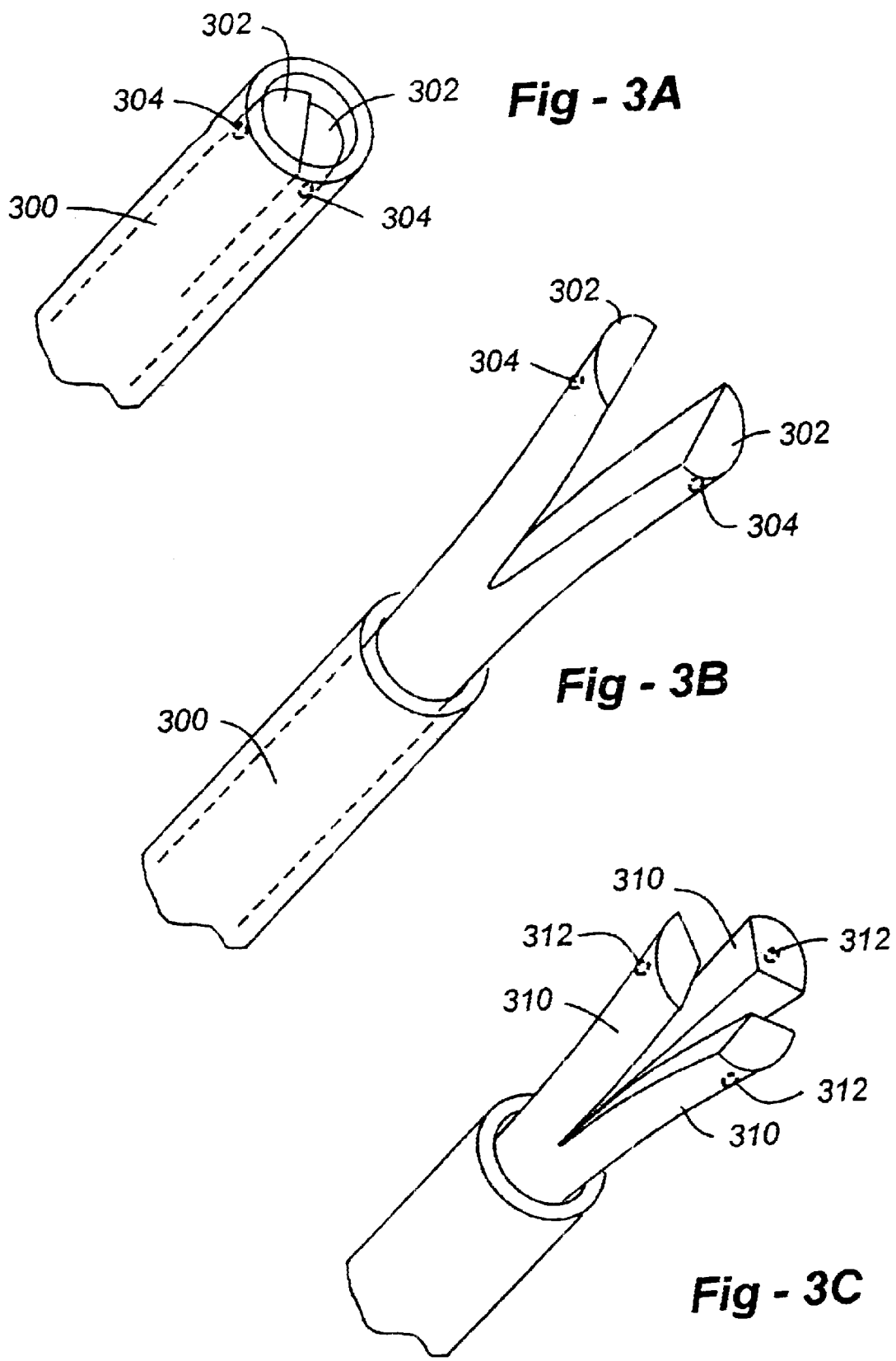

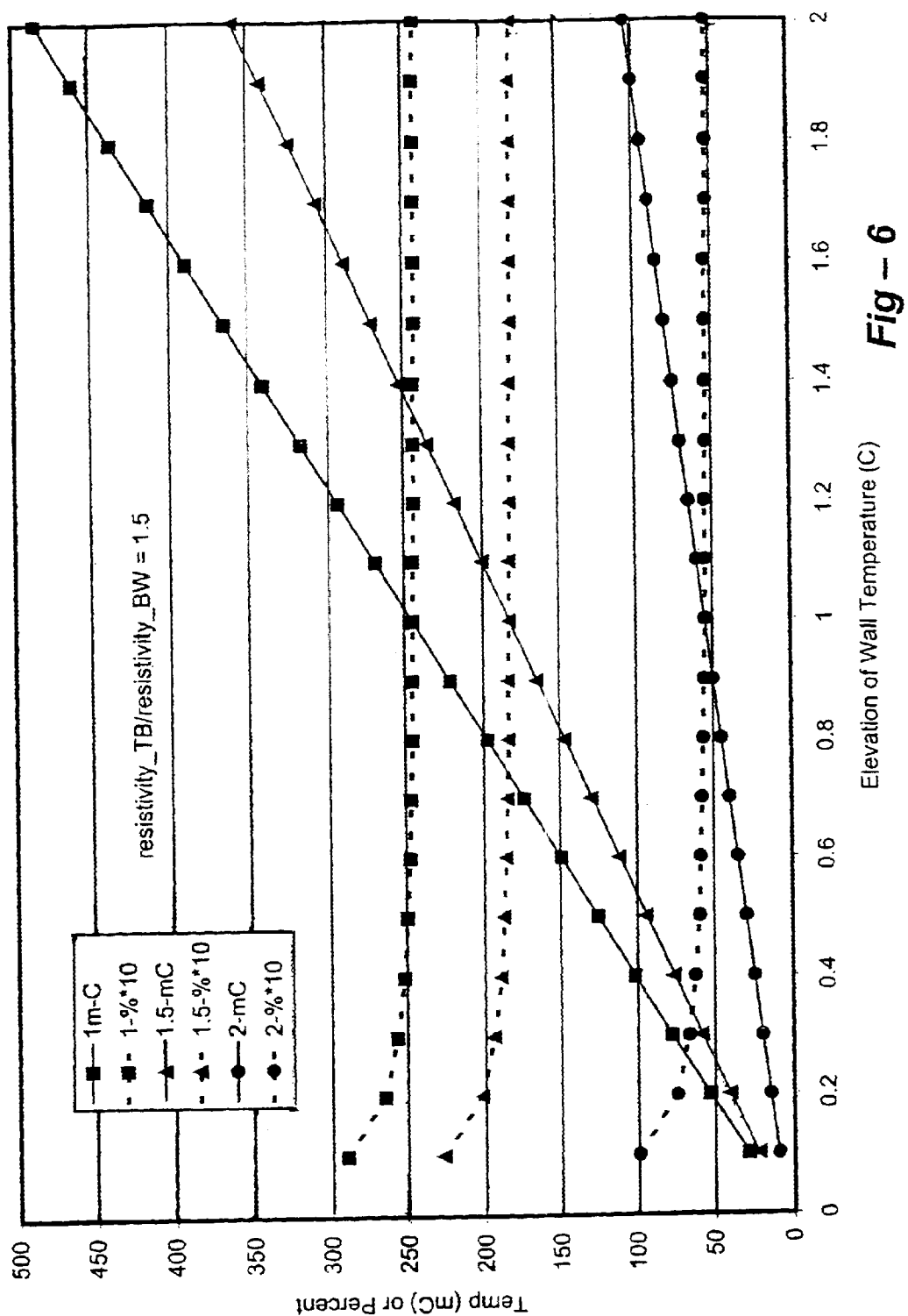

TEMPERATURE SENSING CATHETER

REFERENCE TO RELATED APPLICATION

This application claims priority of U.S. provisional application Ser. No. 60/211,995, filed Jun. 16, 2000, the entire contents of which are incorporated herein by reference.

FIELD OF THE INVENTION

This invention relates generally to medical instrumentation and appliances and, in particular, to a temperature sensor catheter.

BACKGROUND OF THE INVENTION

Arteriosclerosis is a major source of adult morbidity and mortality in industrialized countries. The condition may lead to a number of complications, including coronary thrombosis, myocardial ischemia, unstable angina, myocardial infarction and restenosis of stents and bypass grafts. The classification of atherosclerotic lesions by type can be valuable in predicting clinical complications, and the type of plaque is likely a better predictor of cardiovascular events than angiographic data.

Unstable plaque is well established as producing high risk for sudden myocardial infarction, either through plaque rupture and subsequent thrombotic response, or thrombosis generated at the inflamed surface of the plaque. The rupture of unstable plaque, and the subsequent generation of thrombus, has been estimated to account for 60 to 70% of fatal myocardial infarctions and up to 85% of all myocardial infarctions.

Unstable plaque is characterized by a lipid-rich core, chronic inflammation, fibrous cap, and activated macrophages. Angiography can identify the presence of a ruptured plaque after rupture, but often not before rupture. Thus, it cannot determine the risk associated with a given plaque.

Due to chronic inflammation, the temperature of unstable plaque is typically elevated above that of the adjacent sites on the inner lumen of the vessel. Extensive research has been conducted to confirm the elevated temperatures of unstable plaques, and to develop techniques to clinically identify them. It has been found that there is a correlation between the temperature of atherosclerotic plaque and the vulnerability to blood vessel rupture. In particular, it has been determined that inflamed, unstable deposits typically give off more heat than do healthy, non-inflamed tissues. Accordingly, there have been various apparatus and methods proposed to monitor the temperature of the vessel wall without occluding blood flow. U.S. Pat. Nos. 5,871,449; 5,924,997; and 5,935,075 provide background with regard to the general approach.

To determine that thrombotic events could be predicted through thermal measurements on the plaque surface, Willerson et al. measured the intimal surface temperatures on 20 sites located on 50 samples of excised living carotid artery samples from 48 patients using a thermistor, and then conducted histological studies. The results showed 37% of plaque regions warmer by up to 2.2° C. These warmer regions could not be distinguished from cooler regions by visual observation, but correlated positively with cell density, a marker of inflammation.

Stefanadis et al. conducted human in vivo measurements of plaques using a Betatherm Microchip NTC 100K6 MCD368, 0.457 mm diameter thermistor on the end of a guidewire pressed against the vessel wall by a hydrofoil. They measured thermal heterogeneity of plaque temperatures repeatedly with an accuracy of 0.05° C. and spatial and temporal resolutions of 500 um and 300 ms, in 90 patients with normal coronary arteries, stable angina, unstable angina, and with acute myocardial infarction. This group found artery-wall temperatures that increased progressively from normal patients, to stable angina patients, to unstable angina patients. The measurement of temperature differences in the inner lumen of coronary arteries shows great promise for identifying sites of unstable plaque.

Research on classification of plaque as stable or unstable has been carried out in three main areas: thermal, Ultra-Fast Magnetic Resonance Imaging (MRI) and Intravascular Ultrasound (IVUS), with some work on a few others (e.g. Raman scattering, Optical Coherence Tomography). While MRI and IVUS show promise, only thermal techniques offer a direct, inexpensive method of plaque classification that, due to its minimal hardware and disposable requirements, can be quickly and inexpensively implemented.

Plaque classification by MRI presents numerous obstacles. It brings the problems of requiring a special machine, typically located in other regions of the facility and not available on an ad hoc basis, into the cath lab as questions of plaque stability may arise. The ability of MRI to characterize human atherosclerotic plaque has been investigated by comparing MRI images of carotid artery plaque with histologic examination of the specimens after carotidendarterectomy. The studies indicated that MRI can discriminate the presence of a lipid core and fibrous cap in the carotid artery. The ability of MRI to characterize plaque composition of coronary arteries in the beating human heart has not been demonstrated. Even if the technical challenges of spatial and temporal resolution are solved, the cost of imaging coronary arteries using MRI is likely to be substantial.

While IVUS can accurately identify arteriosclerosis in its early stages, it is much less effective in the classification of plaque by type. Further, IVUS requires expensive and large equipment that also must be brought into the cath lab when needed. The main limitations of IVUS are cost and risk to the patient. IVUS enjoys an installed base in many cath labs, unlike other competing technologies to classify plaque, but it is problematic in this application. IVUS is very operator dependent and typically has a 300 micron resolution, the thickness of the fibrous cap on unstable plaque. Thus, IVUS does not have the needed resolution to identify unstable plaque. Although numerous clinical studies have been performed with IVUS, there are very limited follow-up data to suggest that IVUS examination of a coronary artery can be used to predict the probability that a plaque will rupture.

Yamagishi et al. performed IVUS examination of 114 coronary plaques in 106 patients. During an average follow-up period of 22 months, 12 patients had an acute coronary event related to a plaque that was previously examined by IVUS. Ten of the 12 plaques contained an echolucent zone consistent with a lipid-rich core. Only 4 of 90 sites not associated with acute events had an echolucent zone ($p<0.05$).

Optical Coherence Tomography (OCT) has problems due to its limited penetration distance, and the fact that it requires a saline flush to remove blood from the area and permit transmission of the optical radiation. Further, it can run only at ~5 frames/sec, which will not give good time resolution. This technique, and others, such as pulsed laser radiation and the use of Raman scattering spectroscopy, require the vessel be purged of blood with clear saline for the signals to propagate. Further, they are much less developed than other techniques.

Classification of atherosclerotic plaque stability by measurement of its surface temperature is direct. Due to the chronic inflammation, the surface temperature of unstable plaque is typically elevated above that of the adjacent sites on the inner lumen of the vessel. Measurements in vivo and ex vivo have been made of active plaque sites, with temperature differences from the adjacent normal artery wall ranging up to 2 to 3° C. The equipment associated with thermal measurements may be small and inexpensive, thus easily portable between cath labs or available in all cath labs in a single facility, as opposed to Magnetic Resonance Imaging (MRI) and Intravascular Ultrasound (IVUS). Identification of unstable plaques would permit the cardiologist to decide on treatment on a site-by-site basis during a single catheter insertion.

There are numerous potential treatments for these unstable lesions, including anti-inflammatory and/or antimicrobial treatments, aggressive cholesterol lowering, and heating to generate apoptosis. Stenting techniques are influenced by the classification of the plaque being treated.

Currently, no diagnostic or imaging modality exists that can predict either plaque rupture, hemorrhaging into plaque or plaque erosion in the clinical setting. Hot plaque temperature measurements have been made in research labs and in a few clinical studies, but no such product now exists. Practical and accurate techniques are needed to identify unstable plaque sites in order for these treatment decisions to occur. As classification of plaques becomes established, other therapeutic techniques will develop.

SUMMARY OF THE INVENTION

This invention resides in a thermal sensing catheter (TSC) operative to perform localized temperature measurements, including variations and fluctuations when such measurements are compared to readings taken at different places or at different times. The instrument finds particular utility in detecting and isolating unstable plaque. In the preferred embodiment, miniaturized temperature sensors in the form of microthermistors are embedded into expandable presentation elements disposed at the distal end of the catheter. The sensors may then be deployed to measure the surface temperature of the inner wall of coronary arteries at multiple sites to identify sites of elevated temperature indicative of unstable plaque.

The presentation elements may assume different forms according to the invention, including a "hand" type design and an alternate basket-type structure. In the sensing hand configuration, a plurality (preferably up to 8) of sensors are embedded in the sides of polymeric or metallic sensing arms, which expand out from the centerline of a catheter toward the inner vessel walls. An asymmetric encapsulation technique is preferably used to embed the sensors in close proximity against an outer wall of a sensing arm, while maintaining an insulative backing to reduce the effect of blood temperature on the backside of the arms excessively influencing plaque temperature measurements.

The entire catheter, with thermal sensors and presentation system are preferably disposable. The disposable catheter assembly interfaces to a nondisposable data box receiving signals from the sensing elements. In the preferred embodiment, the data box is a battery-powered, hand-held device, encased in a plastic housing about the size of a pocket calculator. The data box includes a port to which the catheter assembly connects, thereby making electrical contact for ground and the signal lines of each of the individual sensors. The connections from each sensing element are direct; however, in an alternative configuration multiplexing may be used to reduce the number of signal wires.

The data box includes a display to present the calibrated readings from the sensors, as well as memory capabilities to store data for later download through a port incorporated in the housing. The output of the data box is provided to a computer, preferably in real-time and through the same port, to permit full-screen display of the thermal data. In either mode, a full recording of a procedure will be saved for later analysis.

BRIEF DESCRIPTION OF THE DRAWINGS

FIG. 1D shows how the insulting capability of an expanding pad increases with increasing outside diameter (O.D.) for a given sensor size;

FIG. 2A is a drawing which shows a basket-type expandable structure according to the invention in a collapsed state;

FIG. 2B shows the basket-type structure of FIG. 2A in an expanded state;

FIG. 3A shows a second hand-type structure with fingers and sensors disposed in a retracted position;

FIG. 3B shows how the fingers of FIG. 3A expand when the inner structure is pushed out through an outer sheath, thereby causing the sensors to spread relative to one another so as to contact the inner wall of a vessel;

FIG. 3C shows how more than two expanding fingers may be used in conjunction with the design of FIGS. 3A and 3B;

FIG. 4C is a detail drawing of a conical plunger applicable to the invention;

FIG. 5 illustrates an equipment set up applicable to any of the embodiments disclosed herein;

FIG. 6 shows the results of a computer model used to simulate thermal measurement error.

DETAILED DESCRIPTION OF THE INVENTION

Figure 1A:
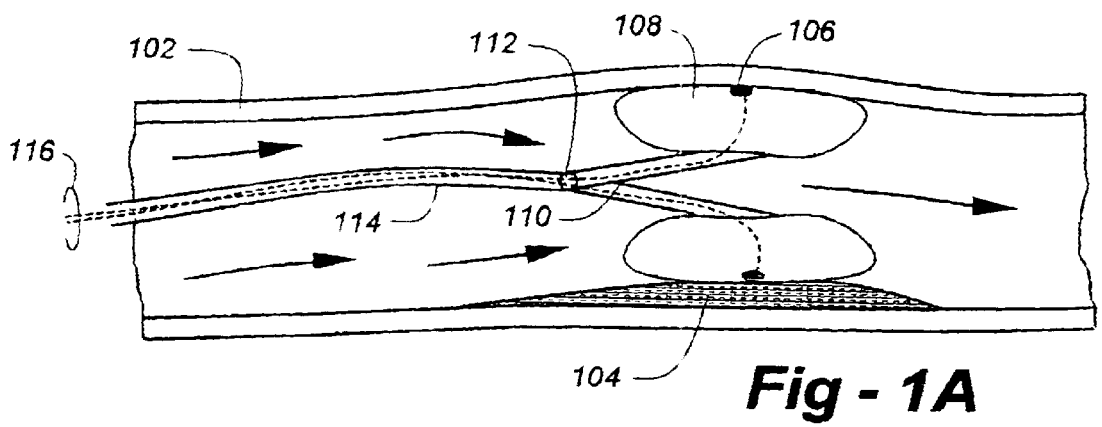
FIG. 1A is a drawing which shows an expanding pad embodiment according to the invention in an expanded state.

This invention is directed to thermal sensing catheter (TSC) configurations. A variety of approaches are described, including improved designs providing additional capabilities, more accurate results, or both. A basic design according to the invention takes the form of a cardiac arterial catheter interfaced to a 'data box' for signal processing, measurement storage and downloading. The distal end of the catheter features a presentation system including a plurality of temperature sensors which preferably make contact with the intimal (innermost) surface of the coronary arteries and facilitate thermal measurements. On the end of the catheter opposite the sensing head there is disposed a controlling mechanism allowing the cardiologist to expand or contract the sensors through the presentation system. The thermal signal data is reduced and displayed via the data box attached to the catheter near the controlling mechanism, either wirelessly or by way of a thin cable.

The catheter itself preferably measures approximately 130 to 150 cm long and approximately 1 to 2 mm in diameter. This diameter is on the order of diagnostic catheters such as IVUS or Doppler. Systems under development, and experimental systems are using 3 to 6 Fr catheters. These small dimensions are well within the precision prototyping and production capabilities of certain suppliers, including Catheters & Disposables Technologies of Minneapolis, Minn. The target spatial and temporal resolution of the device are 500 microns and 50 mC, with a target response time of 100 mS. Sensitivities of non-commercial laboratory experimental systems typically range from 50 mC to 2.5 mC, with spatial resolutions on the order of 500 microns and response times of from 10 mS to 300 mS.

In the preferred embodiment, the invention uses temperature sensors in the form of ultraminiature chip thermistors fabricated using transition metal oxide thermometric media. Useful microthermistors are available from suppliers such as Betatherm of Shrewsbury, Mass., Sensor Scientific of Fairfield, N.J., or Keystone Thermometrics of St. Marys, Pa. The sensors preferably measure a few hundred microns or less in three dimensions leaded with 50-micron wires. Alternatively, however, thermocouples or other devices may be used with thermometric parameters capable of calibration. As such, it should be understood that references to "thermistors" or "sensors" should be interpreted to include all of the alternative device types disclosed herein. In particular, although thermistors based on metal oxide metal oxide media typically exhibit a negative temperature coefficient (NTC), sensor types having a positive temperature coefficient (PTC, wherein resistance increases with temperature) may also be used. PTC devices include, but are not limited to sensors based upon barium and strontium titanate mixtures.

The invention may also make use of resistance temperature detectors (RTDs) such as those employing metal conductors in the form of thin metal wires or thin metal coatings, typically of the PTC type. Such devices typically employ metals such as nickel, tungsten, copper and platinum, conventionally in the form of wire wound around a coil to increase the current path. As a further alternative, the invention may make use of direct detection of thermal black-body radiation of the sensed region, or use a material placed in thermal contact with the sensed region, in any part of the electromagnetic spectrum from DC to ultrahigh frequencies. Optical detection of chemical phase changes may optionally be used, including the technology employed in quartz chemical thermography. As yet a different alternative, physical dimension changes of bulk materials such as mercury or alcohol may be sensed and correlated with temperature.

The circuitry associated with processing the signals from the sensors may be supported in close proximity to the sensors or disposed outside the body, for example, in the data box. Such circuitry may take advantage of standard electronic components, such as transistors, amplifiers, or diodes, with or without on-chip compensating circuitry. Specialized integrated circuits may also be used, for example, where the temperature sensing is comprised of microelectromechanical systems (MEMS) devices, such as oscillators, filters or mixers based on oscillating microstructures such as beams, combs, disks or other structures employed to perform the role of conventional microelectronic components.

As a further option, phase-transitions of liquid crystals may be used as temperature sensing elements according to the invention. Such materials possess liquid properties but also exhibit the properties of a crystal, and are known to produce a change in color or transmissivity with temperature. Other chemicals that exhibit changes in spectral absorption (color), polarity, or other configurations with temperature may alternatively be employed. In all arrangements where transmissivity, reflectivity, polarization or other wave-form altering characteristics are employed, electromagnetic transmitters and receivers may be used to detect these changes. The detectors themselves may be constructed from at least the following types of materials: cadimum sulfide (CdS); photomultiplier tubes; diode detectors; thermal bolometers. Chemical detection of electromagnetic radiation, such as silver nitrate may further be used and the electromagnetic radiation may be in any regime of the spectrum from DC to ultrahigh frequencies Apart from sensor type, the invention makes use of a "presentation system" operative to place the sensors in contact or thermal proximity to the vessel wall. In the preferred embodiment, the presentation system includes a set of articulating "sensing fingers" forming a hand-shaped structure. Each finger is capable of presenting a thermal sensor radially from the catheter up against the vessel wall. In an alternative embodiment, the thermal sensors are supported on an expanding basket structure. The hand-type structure will be described first, followed by the basket structure. Details of the data box will then be provided.

FIGS. 1A through 1D illustrate a first hand-type embodiment according to the invention based upon an expanding pads which provide enhanced insulation. The use of padding permits close contact of the thermal sensors, while insulating from the thermal affects of flowing blood. As such, blood flow in the artery is restricted, but not terminated. The stress on the artery walls is also lessened as compared to the stress imposed by inflating balloons of prior-art devices.

Figure 1B:
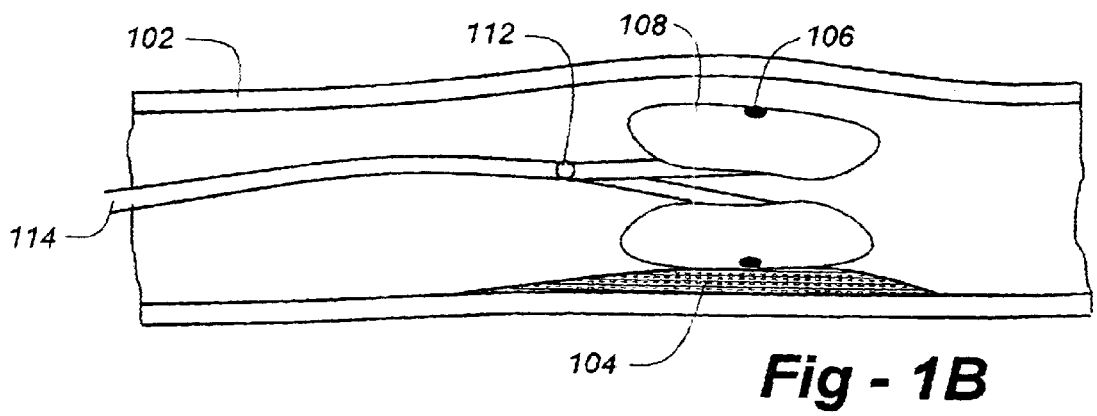
FIG. 1B shows the distal end of the arrangement of FIG. 1A in a collapsed state.
Figure 1C:
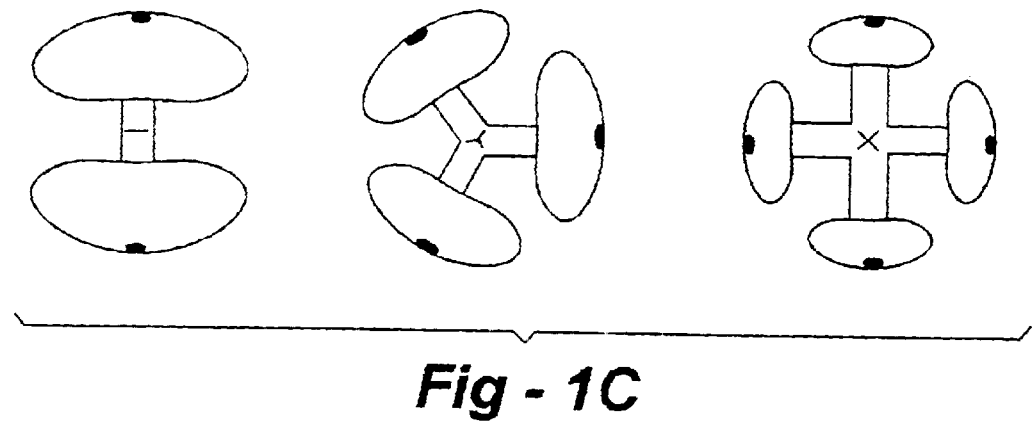
FIG. 1C shows how the invention may use multiple expanding pads beyond a pair of pads.

FIG. 1A shows this embodiment with the padded fingers in an expanded configuration to detect unstable plaque 104 on the wall of a vessel 102. Preferably, the pads 108 connect to cantilevered arms 110 which pivot at a point 112. The point 112, in turn, as connected to a central guide 114 which carries wires 116 to the sensors 106. FIG. 1B shows the distal end of the arrangement in a collapsed state, that is, wherein the pads 108 are pivoted down toward one another, allowing the device to be compacted into a compressed form for insertion into a region to be probed. Having found an area to be examined, the pads are expanded gently at various positions to take measurements of the opposite inner walls of a vessel lumen, as shown in FIG. 1A.

As shown in FIG. 11C, the invention in this case is not limited to a pair of pads with sensors, but may use fewer or more such as three, four, or more. FIG. 1D shows how the insulating capability of an expanding pad increases with increasing O.D. for a given sensor size owing to the preferred asymmetric placement of the sensors within the expandable elements. In particular, given a thermistor having dimensions on the order of 150 by 280 microns, the sensors are relatively close to the central lumen in the case of a 1-mm O.D. catheter whereas, for a 2-mm catheter, a substantial amount of insulating material is available. The effect of this is to increase the thermal resistance between the thermal sensor and the flowing blood as the outer diameter of the sensing head is increased, while maintaining a constant and low thermal resistance between the thermal sensor and the outer surface of the sensing arm, where it contacts the inner wall of the vessel.

To expand and/or contract the structure just described, or the other structures described elsewhere herein, various principles may be used according to the invention, including shape-memory alloys and/or a guide wire which is pulled or pushed. If a shape-memory material is used, the structure may include a temperature generator causing the arms or other elements to expand and contract using an appropriate thermal mechanical material.

FIGS. 2A and 2B illustrate an expanding basket embodiment of the invention in a collapsed and expanded condition, respectively. In this configuration, a central lumen 202 surrounds a filament 204 movably engaged therewithin, such that by pulling on the filament 204, a basket-like structure at the distal end of the arrangement is caused to open, thereby urging sensors 210 located on the expanding arms to move outwardly, and against an area of the inner wall of a vessel under investigation. Note that the space 212 allows blood flow past the instrument even with the basket in the expanded condition. On this and all of the embodiments disclosed herein, one or more sensors such as 220 may further be positioned on a non-expanding portion to take a reading of blood flow temperature or other ambient conditions.

One advantage of this and other embodiments disclosed herein, is that the structure may be produced with sufficient accuracy that the pulling on the filament 204 in the expansion of the basket may be calibrated relative to one another, so that with gradations at the proximal end at which point the filament is pulled, an estimate of the expansion of the basket, and therefore an estimate of the inner diameter of the vessel may be ascertained from outside the body. More particularly, with sufficiently sensitive temperature sensors, the system will notice a slightly different temperature when the sensors begin to touch the walls of the vessels as opposed to when exposed to blood flow. This difference in temperature may be used as an indication of when the expanding arms have reached the vessel walls, thereby giving an accurate estimate of inner diameter as well as surface temperature, particularly with a calibrated system.

As with the padded structure described with reference to FIGS. 1A–1D, the material forming the basket onto which the sensors 210 are placed or embedded is preferably sufficiently insulated that blood flow past the device does not compromise the reading of the inner wall temperatures. Another advantage of this particular structure is that, being symmetrical forwardly and rearwardly of the sensors, even with the basket in an expanded position, the device may be moved forward and backward, which may be particularly advantageous in an area benefiting from closer scrutiny.

FIGS. 3A through 3C illustrate a second hand-type structure according to the invention, wherein fingers 302 slidingly disposed within an outer sheath 300 are used to place sensors 304 in contact with a surface to be tested. FIG. 3A shows the structure with the fingers 302 and sensors 304 disposed in a retracted position. FIG. 3B shows how the fingers expand when the inner structure is pushed out through the sheath 300, thereby causing the sensors 304 to spread relative to one another so as to contact the inner wall of a vessel. Such spreading is preferably accomplished through a pre-established bend or shape-memory material or alloy, which naturally expands to a previously determined amount as the device is pushed out through the sheath 300.

As with other embodiments described herein, the presentation elements are preferably cantilevered to provide a constant, predetermined force such that even in the fully deployed condition, the pressure against the inner wall of the vessel is below that wherein damage may occur.

As with the other embodiments disclosed herein, preferably the materials 302 forming the arms in this case are insulated against blood flow temperature variations so that the sensors 304 accurately record wall temperatures without being adversely affected by blood flow. This embodiment is also not restricted to the use of two fingers, but more may be used such as the three fingers 310, each with a sensor 312, as shown in FIG. 3C. In addition, as with the other embodiments described herein, the embodiment described with reference to FIGS. 3A through 3C may also be calibrated so as to provide a user with an estimate of inner vessel diameter as well as localized temperature.

Figure 4A:
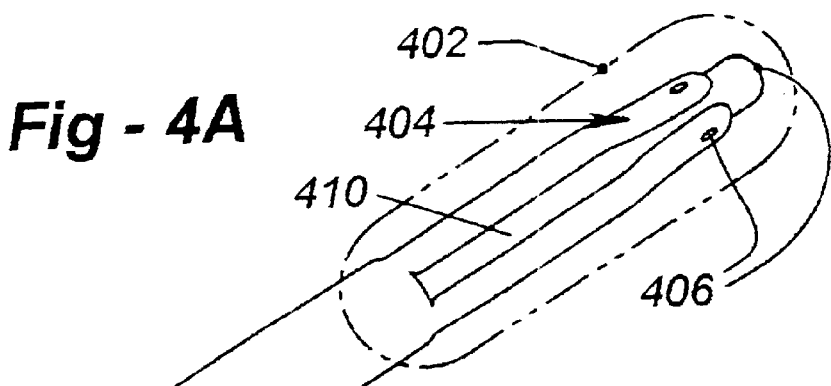
FIG. 4A illustrates a preferred hand-type embodiment of the invention in a contracted condition, including a sensing head with one or more sensing arms, each with a thermal sensor, which are expanded by pulling a central member.
Figure 4B:
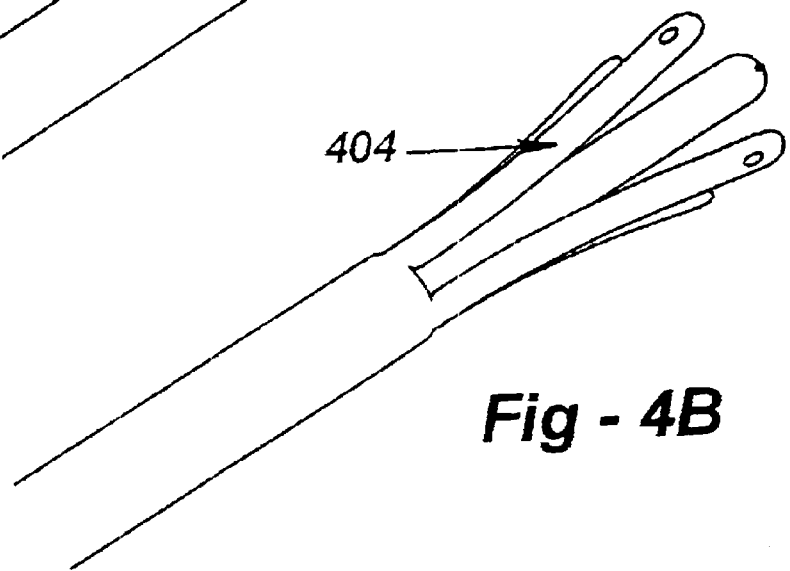
FIG. 4B illustrates the embodiment of FIG. 4A in an expanded state.

FIGS. 4A through 4D preferred hand-type embodiments of the invention. In FIG. 4A, a sensing head 402 includes one or more sensing cantilevered arms 404, each with a thermal sensor 406, surrounding a central member 410. The arms and central member are configured such that when the member is pulled from the proximal end, the arms fan outwardly from the contracted state of FIG. 4A into a the expanded position, as shown in FIG. 4B. Again, the arms are cantilevered to provide a relatively constant and uniform force against the vessel wall in the expanded state while avoiding excess pressure.

Figure 4D:
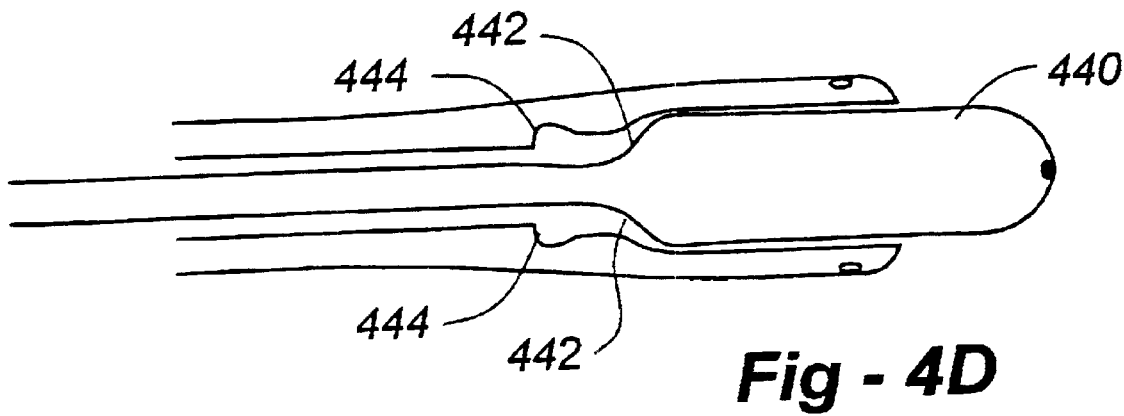
FIG. 4D is a drawing of a central lumen configuration incorporating an inner lip providing a rapid yet controlled flare of the expanding arms.

In FIGS. 4A and 4B, the member 410 is preferably not uniform in cross section but, rather, includes a conical or ramp shape along the distal end of the member, such that when it is pulled from the proximal end the arms fan outwardly and into the sensing position shown in FIG.4B. FIG. 4D is a drawing of a central lumen configuration incorporating an inner lip providing a rapid yet controlled flare of the expanding arms. In this case the proximal end of the plunger 440 includes a rim 442 configured to lock into a corresponding recess 444 in the body of the sheath. This allows the arms to expand outwardly while preventing over-expansion.

FIG. 4C is a detail drawing of a preferred embodiment wherein the central member assumes the form of a conical plunger 420 connected to a cable 422 which runs down a hole central to the body of the sensing head (not shown). The sensing arms 424 preferably include chamfered ends 426 which help to expand the arms when the plunger 420 is pulled inwardly from outside the body. As with the other embodiments disclosed herein, slots 428 may be molded in the outer surfaces of the sensing arms to receive the temperature sensing elements. Such slots may run the entire length of the catheter, thereby creating a channel for the electrical leads. The sensors are preferably embedded in the distal ends of the grooves and encapsulated as described elsewhere herein.

In terms of construction, thermoset polymeric casting techniques employing fluoropolymeric molds are preferably used to construct the sensor presentation system. Alternative casting and mold materials and techniques may be used, including thermoplastic polymers such as polyvinyl chloride or polyethylene. Production of such molds is currently carried out through micro-machining; however, electric discharge machines (EDM) may be employed for greater mold cavity resolution.

Using specialized packaging, a plurality of sensors (preferably 4 to 8) are embedded in the sides of polymeric or metallic sensing elements, out from the centerline of the catheter toward the inner vessel walls. An encapsulation technique is used to embed the thermistors close against an outer wall of a sensing arm, while maintaining an insulative backing to reduce the effect of blood temperature on the backside of the arms excessively influencing plaque temperature measurements.

The sensors may be cast into the arms using successive layering of material in the molds. As an alternative, the sensors and lead wires may be disposed in grooves cast into the sensing arms and subsequently sealed. Any support coatings must be extremely thin in order to not interfere with the placement of the thermistor very near the edge of the sensing arm to reduce thermal resistance between the thermistor and the surface of the plaque. Ultrathin coating techniques such as Paralyene, physical vapor deposition, or other thin but strong coatings will be explored to support the lead connections during fabrication of the sensing arms or other expanding elements.

The sensing arms may be comprised of a elastomeric, polymeric, metallic or other material exhibiting a high thermal resistivity and whose modulus of elasticity is such that a small and uniform force can be applied against the inner wall of the vessel by the extended arms. This will be achieved by extending the arms radially outward from the central axis of the catheter and sensing head to a point somewhat beyond the point at which the tips of the sensing arms first contact the inner vessel wall. This will pre-load slightly the tips of the arms against the inner wall of the vessel and maintain a constant contact with the inner wall of the vessel as the sensing head is drawn back down the vessel. The degree of preloading must be such that constant gentle contact with the vessel wall is maintained, but not so much that damage occurs to the intimae of the artery.

The temperature sensors are preferably embedded slightly below the outer surfaces of the sensing arms or elements, along the surface closest to the inner wall of the vessel. The material covering the thermal sensor on the outer surface of the expanding element is chosen and configured so as to permit minimal thermal resistance between the thermal sensor and the outer surface of the sensing arm. This may be achieved by having a minimal thickness of material, or by choosing a material of low thermal resistance. In contrast, the bulk material of the expanding element is preferably chosen to have high thermal resistance and to be of a significantly greater thickness than the thickness of the material covering the thermal sensors on the outer surface of the sensing arms.

In the preferred embodiments, the total thermal resistance of the body of the sensing arm or element (i.e., between the thermal sensor and the flowing blood contacting the inner wall of the sensing arm) will be significantly greater than the total thermal resistance of the material covering the thermal sensor on the outer surface of the sensing arm. As such, when the sensors are deployed radially outward to make a vessel wall temperature measurement, the thermal sensor will be in significantly better thermal contact with the inner wall of the vessel than with the flowing blood.

Thus, through choice of configuration and material, the error introduced in the vessel wall temperature measurement by the flowing blood will be minimized. This is critical to the adequate operation of the sensing head since the blood will have up to about a 2 degree centigrade temperature differential from the vessel wall temperature. In addition, the flow of the blood will assist in establishing a greater thermal gradient, and hence heat flow, on the inner surface of the sensing arm.

When the measurements are made, a baseline is taken by drawing the sensing head along a section of normal artery. These delivery catheters will locate the sensors axially in the artery under control of the cardiologist, who will then present them radially out against the lumen wall. When extended, the elastomeric elements exert a slight spring force against the endothelial wall to ensure contact. Potential thermal interference from non-vascular heat generating foci, such as a pacemaker/defibrillator generator or prior stents would not represent significant measurement errors, as these devices would appear on angiogram and thermal measurements proximate to them avoided.

The catheters will locate the sensors axially in the artery under control of the cardiologist, who will then present them radially out against the lumen wall. When the measurements are made, a baseline will be taken by drawing the sensing head along a section of normal artery. When extended, the cantilevered elastomeric arms or basket elements exert a slight spring force against the endothelial wall to ensure contact. It is also possible that the arms will always be extended to their maximum extent, in which case the force on the arterial wall will preferably be determined by the cantilevered (i.e., elastomeric) arms.

FIG. 5 illustrates an equipment set up applicable to any of the embodiments disclosed herein. The sensing head with thermal sensors is connected to a disposable catheter 506 which, in turn, is coupled to a data unit 520 having a display 522 and an output such as a serial output to a personal computer. Between the junction 510 at the data unit 520, there is preferably disposed a manually operated expansion control 508, providing hand-operated controls to expand the sensors of the catheter at the thermal head 502.

The nondisposable data box 520 is preferably a battery-powered, hand-held device, encased in a plastic housing about the size of a pocket calculator. It will have a port to which a line from the TSC will connect, making electrical contact for ground and the signal lines of each of the individual sensors. Signal multiplexing may be used in the catheter to reduce the number of signal wires entering the data box.

The LCD 522 presents the calibrated readings from the sensors. Memory capabilities may be added to store data for later download through the data port incorporated in the housing. The data box will preferably be configured to supply its output to a PC in real-time through the same port, thereby permitting full-screen display of the thermal data. In either mode, a full recording of a procedure will be saved for later analysis. This device will sit outside the sterile field, and will thus not be required to undergo sterilization procedures.

Computer models were run to simulate the predicted thermal measurement error when the sensing head measured the temperature of the inner wall of the vessel. The temperature differential to be measured was varied in the model from 0 to 2° C. above the temperature of the flowing blood. It was assumed that the specific bulk thermal conductivity of the resin of the sensing arm was 1.5 times that of the material covering the thermal sensor on the outer side (the side directly contacting the inner vessel wall).

FIG. 6 shows the results of the computer model. Three cases were modeled: sensing head diameter of 1 mm, 1.5 mm and 2 mm. It can be seen that the measurement error falls dramatically from a maximum of about 500 mC (about 25% of the measured temperature difference) for the 1 mm diameter sensing head to about 100 mC (about 5% of the measured temperature difference) for the 2 mm diameter sensing head.

Individual sensing arms were fabricated to demonstrate the differential temperature measuring accuracy effect achieved through the asymmetric placement of thermal sensors in the sensing arms. These prototypes were fabricated at many times full-size in order to quickly permit reduction to practice of the concept.

Experiments were run with these sensing arms. They were first equilibrated to room temperature (~20 C.), then calibrated through complete encapsulation in an elevated temperature media (~37 C.). They were then held in contact with a cold surface (~0 C.), first with the proximal surface (the surface with the thermal sensor closest to it) contacting the cold surface, and then with the distal surface (the surface with the thermal sensor farthest from it) in contact with the cold surface. This was followed by a second calibration, and finally with equilibration to room temperature.

Figure 7:
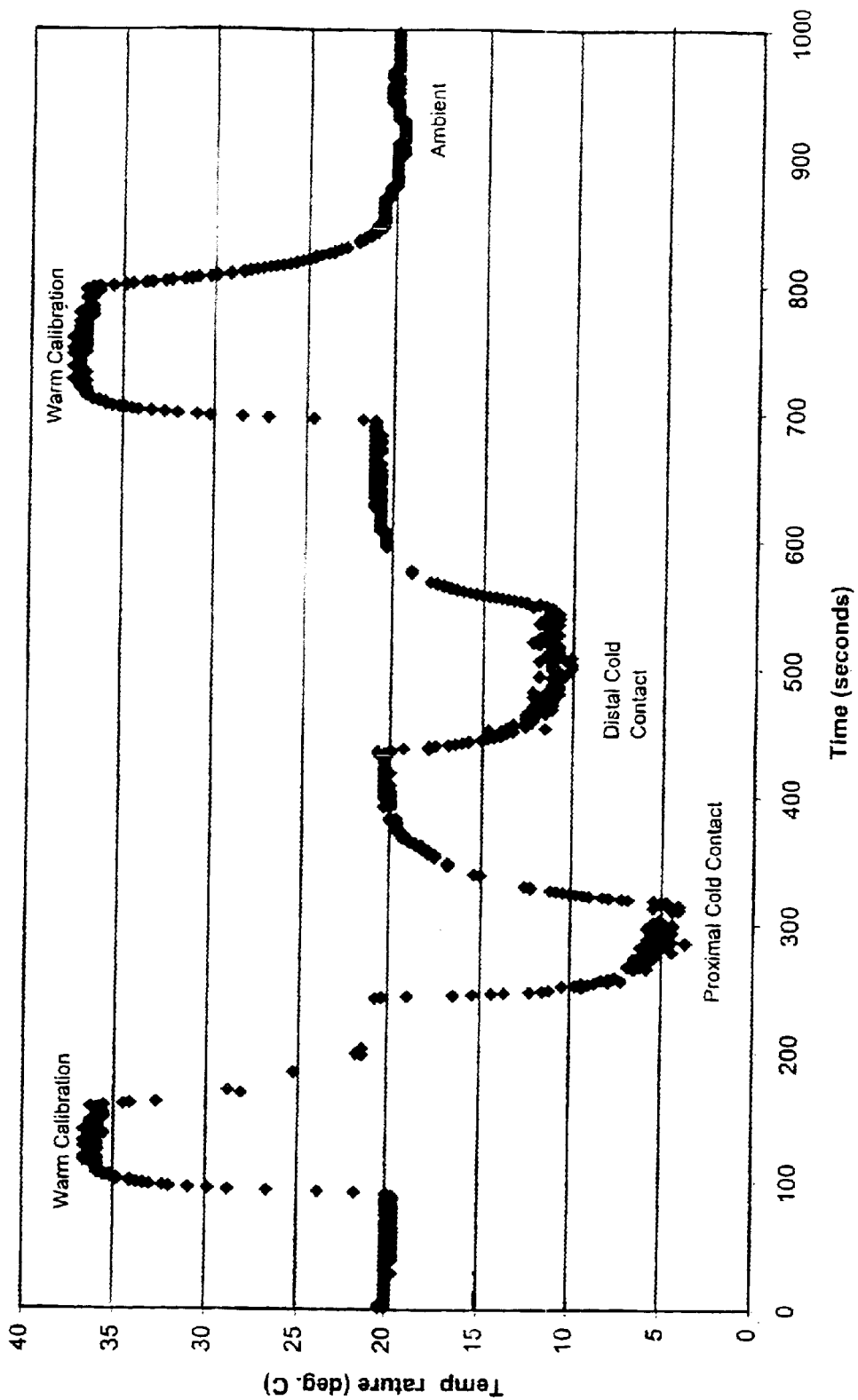
FIG. 7 shows the results of a sensing arm experiment.

The results of one run of these experiments, shown in FIG. 7, clearly illustrate the increased sensitivity of the sensing arm to temperatures presented on the proximal side where the thermal sensor has the least thermal resistance between itself and the surface being measured.

Although the system described herein is ideally suited to plaque temperature sensing catheter designs, the same platform technology may be used to detect inflamed or malignant cells during other procedures, including laparoscopy, gastrointestinal endoscopy, ophthalmoscopy, arterography, and transcranial imaging. Other cardiovascular pathologies (e.g. myocarditis, valvulitis, aortitis) might also be detected by using this device. Furthermore, as an alternative to electrical signal encoding, wide-angle fiber-optic technology may permit the production of a miniature fiber-optic probe that could be incorporated into the treatment catheter.

We claim:

1. A system for sensing the temperature of the wall of a vessel or an arterial wall, comprising:
    an elongated catheter having a distal end and a proximal end;
    a sliding filament that protrudes from both ends of the catheter, the protruding filament at the proximal end of the catheter acting as a manually operated expansion control;
    a temperature sensing tip including a plurality of presentation elements in the form of cantilevered fingers at the distal end of the catheter which expand outwardly by pulling on the manually operated expansion control, each element having a temperature sensor supported thereon which is adapted to be placed in contact or immediately proximate to the vessel wall during the expansion; and
    a data unit operative to receive signals from the temperature sensors and display information indicative of vessel wall temperature as sensed by the sensors.

2. The system of claim 1, wherein the cantilevered fingers are configured to provide are relatively constant and uniform force against the vessel wall.

3. The system of claim 1, wherein the fingers surround a central plunger coupled to the manually operated expansion control, such that pulling on the plunger causes the fingers to expand outwardly and pushing on the plunger causes the fingers to turn to a contracted position.

4. The system of claim 3, wherein the plunger is conically shaped.

5. The system of claim 3, wherein the fingers include an inner lip configured to engage with the plunger to protect against over-spreading of the fingers.

6. A system for sensing the temperature of a vessel wall or an arterial wall, system comprising:
    an elongated catheter having a distal end and a proximal end;
    a sliding filament that protrudes from both ends of the catheter, the protruding filament at the proximal end of the catheter acting as a manually operated expansion control;
    a temperature sensing tip including one or more presentation elements, each element having a temperature sensor supported thereon;
    each presentation element having a proximal end coupled to the distal end of the catheter and a distal end coupled to the distally protruding end of the filament such that pulling on the manually operated expansion control causes each element to move from a retracted position to an expanded position enabling the sensor to be placed in contact or immediately proximate to the vessel wall, and pushing on the manually operated expansion control causes each presentation element to return to the retracted position from the expanded position; and
    a data unit operative to receive electrical signals from the temperature sensors and display information indicative of the physiologic temperature of the vessel wall.

7. The system of claim 1, wherein the temperature sensors are thermistors.

8. The system of claim 1, wherein the presentation elements are thermally insulative so that the sensors are isolated from temperature fluctuations caused by blood flow or other ambient conditions.

9. The system of claim 1, wherein the presentation elements are configured such that blood continues to flow around the elements when the elements are in the expanded position.

10. The system of claim 1, wherein the temperature sensing tip features a plurality of longitudinal slices forming a basket structure which flares out when the manually operated expansion control is pulled, and which collapses when the control is pushed.

11. The system of claim 1, further including at least one thermal sensor to measure a non-wall temperature.

12. The system of claim 1, wherein the presentation elements include an outer longitudinal groove into which the temperature sensors are embedded.

13. The system of claim 12, wherein the temperature sensors are hardwired to the data unit, and the groove extends the length of the catheter to receive the wires.

14. The system of claim 1, wherein the catheter is disposable.

* * * * *

UNITED STATES PATENT AND TRADEMARK OFFICE
CERTIFICATE OF CORRECTION

PATENT NO. : 6,712,771 B2
DATED : March 30, 2004
INVENTOR(S) : Thomas F. Haddock and William W. O'Neil It is certified that error appears in the above-identified patent and that said Letters Patent is hereby corrected as shown below:

Column 12,
Lines 33, 35, 39, 43, 48, 50 and 56, replace "claim 1" with -- claim 6 --.

Signed and Sealed this

First Day of February, 2005

JON W. DUDAS
*Director of the United States Patent and Trademark Office*